United States Patent [19]
Moschik

[11] Patent Number: 5,653,588
[45] Date of Patent: Aug. 5, 1997

[54] PLASTIC ORTHODONTIC COMPONENT PART AND METHOD OF FORMING

[75] Inventor: Erich Moschik, North Wilmington, N.C.

[73] Assignee: CDB Corporation, North Wilmington, N.C.

[21] Appl. No.: 454,941

[22] Filed: May 31, 1995

[51] Int. Cl.⁶ .................................................. A61C 3/00
[52] U.S. Cl. .................................................. 433/8; 433/9
[58] Field of Search .................................................. 433/8, 9

[56] References Cited

U.S. PATENT DOCUMENTS

| | | |
|---|---|---|
| 1,976,141 | 6/1934 | Richardson . |
| 2,045,025 | 6/1936 | Richardson . |
| 4,302,532 | 11/1981 | Wallshein . |
| 4,322,206 | 3/1982 | Reynolds . |
| 4,430,061 | 2/1984 | Webb et al. . |
| 4,604,057 | 8/1986 | Viglietti . |
| 4,954,080 | 9/1990 | Kelly et al. . |
| 5,254,002 | 10/1993 | Reher et al. ................... 433/8 |
| 5,267,854 | 12/1993 | Schmitt ........................ 433/8 |
| 5,318,440 | 6/1994 | Adam et al. ................... 433/8 |
| 5,322,435 | 6/1994 | Pletcher ....................... 433/8 |
| 5,429,499 | 7/1995 | Semetz ........................ 433/8 |

FOREIGN PATENT DOCUMENTS

2662070  11/1991  France ........................ 433/8

Primary Examiner—Nicholas D. Lucchesi
Attorney, Agent, or Firm—Collard & Roe, P.C.

[57] ABSTRACT

The present invention relates to an orthodontic component part made of a plastic, which consists of a thermoplastic or a thermoset plastic which is cured to a great extent and by means of which the polyaddition is terminated at least at body temperature.

16 Claims, 8 Drawing Sheets

PLASTIC ORTHODONTIC COMPONENT PART AND METHOD OF FORMING

BACKGROUND OF THE INVENTION

1. Field of the Invention

The invention relates to an orthodontic component part, for example a bracket made of plastic, as described in the generic term of claim 1 and a method for the production of said component part.

2. The Prior Art

In a known orthodontic device—according to U.S. Pat. No. 1,976,141 and U.S. Pat. No. 2,045,025, the tooth attachments are made of stainless steel and secured to a stainless steel band which encircles the tooth to hold the tooth attachment in the appropriate position.

Various other tooth alignment methods and orthodontic devices have been developed in which stainless steel tooth attachments are cemented directly to the surface of the tooth. These methods and devices require no band to secure the tooth attachments. Such systems are often used. Inter alia, these known tooth alignment methods and devices are disclosed in U.S. Pat. Nos. 4,604,057, 4,430,061 and 4,322,206. The metallic appearance of such stainless steel tooth attachments is a significant drawback. Therefore, for reasons of appearance, in particular adult patients desire orthodontic devices, which are not made of metal but of transparent or translucent materials as such materials provide improved cosmetic appearance. Accordingly, transparent plastic materials are used, mostly polycarbonates or transparent or translucent ceramic materials of aluminum oxide. In known tooth attachments, which consist of non-metallic materials and are produced in very small sizes to keep cosmetic drawbacks at a minimum, it is known—according to U.S. Pat. No. 4,302,532 — that the strength of ceramic tooth attachments of plastic materials is increased by reinforcing elements.

Furthermore, orthodontic devices with a ceramic tooth attachment consisting of a polycrystalline ceramic structure with various additives, are also known. A known ceramic tooth attachment—according to U.S. Pat. No. 4,954,080—consists of polycrystalline ceramics with a light transmission in the visible spectrum, which reduces the visibility of this tooth attachment, so that when it is mounted on the tooth, it can be hardly recognized by a third party. This polycrystalline ceramic body for the ceramic tooth attachment is produced by pressing powdered high purity aluminum oxide, which is then sintered to present a close to zero porosity and an average grain size in the range of 10 to 30 micrometers. Preferably, the tooth attachment should be colorless. An in-line light transmission in the visible spectrum should be 20 to 60% through a specimen having a thickness of 0.5 mm. The drawback of this tooth attachment is that it cannot be seen when X-rays are made.

However, it is already known—according to EP-B-O 189 540—that microfilled dental material is being manufactured which presents both, good X-ray opaqueness and simultaneously good transparency. This dental material which is used as filling material, dental cement, crown and bridge material, prothetic material and also for the production of dentures, inlays, implantations and prefabricated parts, consists of polymerized inorganic binders and compositions of rare precious metals and also, if required, further inorganic compositions as filling materials, whereby it may also contain a fluorinated rare earth-metal (elements of atomic number 57–71 of the periodic table of elements) or a mixture of these fluorides. This type of dental material is often mixed to a paste by kneading, which hardens under various conditions, in particular under the effect of light. The light transmission in the visible spectrum for such parts is in most cases enough, however, when used for tooth attachments and orthodontic devices it was not satisfactory.

SUMMARY OF THE INVENTION

The object of the present invention is to create an orthodontic component part and encompasses a method for the production of said part, which allows for a cost-effective and individual production of different brackets. Moreover, it is also possible to manufacture different moulds for such component parts or respectively brackets at relatively low costs.

The object of the present invention is to achieve by selecting the plastic that no change in the state of the material of the bracket takes place when the latter is used, in particular in orifices of the body, such as the mouth. This way, by using modern plastic materials, such a plastic bracket has hardnesses which can be compared to those of aluminum oxide component parts. By using plastic materials it is also possible in a simple manner to modify tools and thereby also the shape of orthodontic component parts.

Another object of the invention is that the cross-linking of the thermoset plastics does not permit a subsequent change of the plastic material, whereby there are no negative effects for people because of the use of polyurethane and because polyurethane is also resistant against the aggression of various liquids which appear in the mouth for example.

A further object of the invention is to achieve particularly high-strength parts.

An improved regulation of the teeth is achieved by a further object, in particular if the orthodontic component part is a bracket, since the positioning of the tooth due to the pressure applied by the tensioning wire is not obstructed by friction between the component part and the tensioning wire. Moreover, good adhesion and a tight connection is achieved between the lining element and the orthodontic component part.

High strengths and no side-effects in the mouth of the user are achieved by another object of the invention.

A further object of the invention is on the one hand to achieve a tight fitting and a greater durability of the contact surfaces facing towards the tooth surface and on the other hand, to be able to loosen the orthodontic component part without destroying the tooth surface.

A further object of the invention is a method which provides very tight and void-free component parts with simple means and by using cost-effective molds. This permits not only a rapid adaptation of the outer shape of the bracket but also a cost-effective production with simple processing steps, which allows for the manufacture of cost-effective but very resistant orthodontic component parts.

Other objects, advantages and features of the present invention will be apparent from the following detailed description when read in conjunction with the drawings and the appended claims.

BRIEF DESCRIPTION OF THE DRAWINGS

The invention is explained hereinafter in further detail, by way of example only, of the accompanying drawings, in which.

DETAILED DESCRIPTION OF PREFERRED EMBODIMENTS

Figure 1:
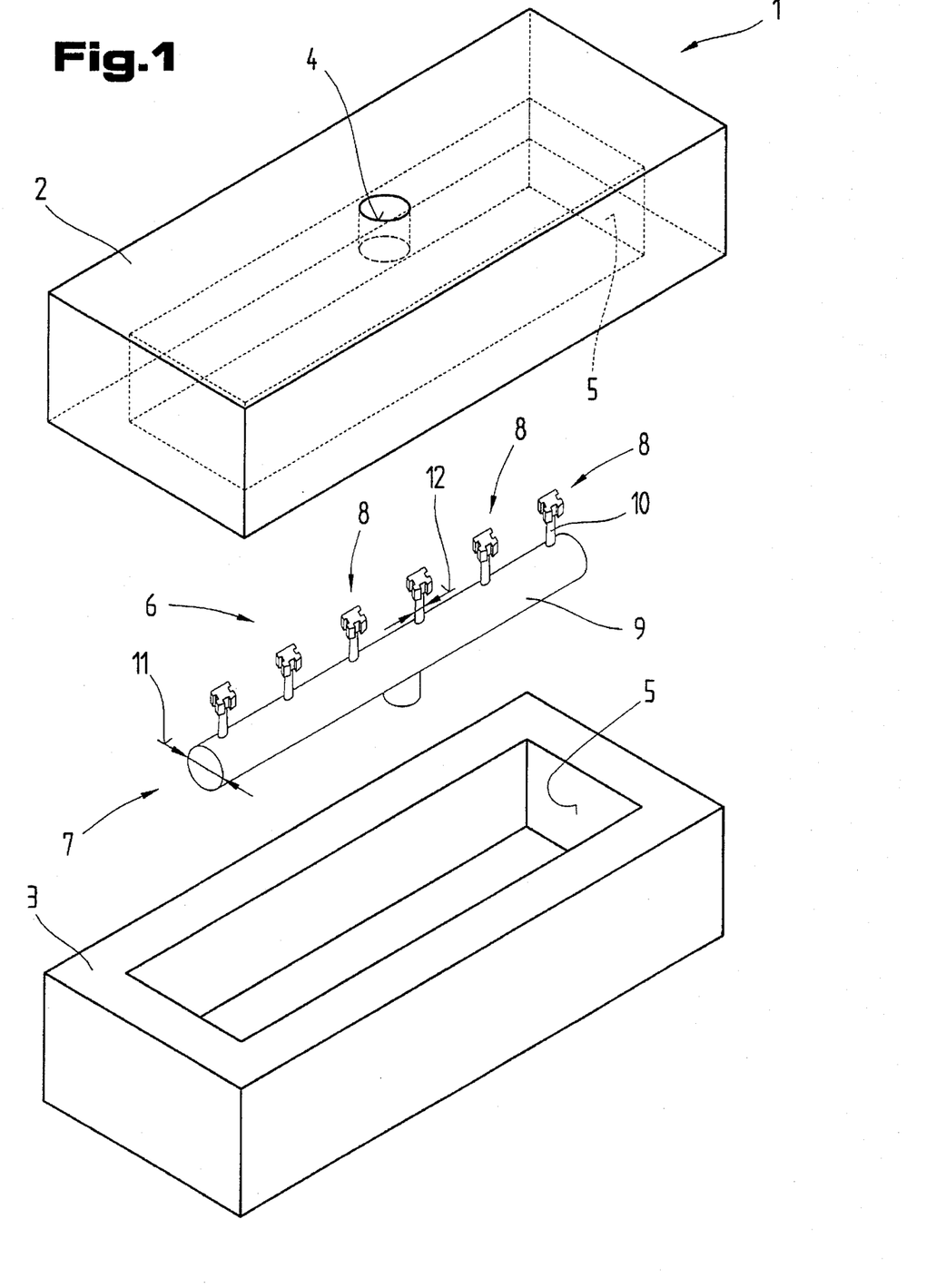
FIG. 1 is a simplified exploded representation, in perspective, of a green model for orthodontic component parts with the associated forming case.

FIG. 1 shows a forming case 1 comprising a male mould 2 and a female mould 3 and a sprue inlet 4 arranged in the male mould 2, which ends in a mould cavity 5 of the forming case 1.

Furthermore, FIG. 1 shows a green model 6 needed for the production of the casting mould, which consists of a sprue channel model 7 and at least one reference component part 8 arranged thereon. Thus it is possible for example to create the entire green model 6, or respectively individual parts thereof, from a master model, and/or to use as green model 6, or respectively also individual parts thereof, already a replica from the master model. The sprue channel model 7 on the other hand, consists of a distribution channel model 9 and a supply channel model 10, each of which is associated with the reference component part 8. Thereby, the distribution channel model 9 has a greater diameter 11 than a diameter 12 of the supply channel model 10. This way, as described hereinafter in more detail, it is ensured that the casting material can be distributed without great resistance within the casting cavities of the mould, which are formed by the sprue channel model 7.

The reference component part 8 can be precisely prefabricated in the desired shape and thus, can be connected at a minimal connection point to the supply channel model 10, for example by bonding, welding, etc. The reference component part 8 corresponds in its outer shape precisely to the orthodontic component part to be produced. To produce this reference component part 8, different materials can be used such as metal, nonferrous metal, plastic, plaster or wood.

Figure 2:
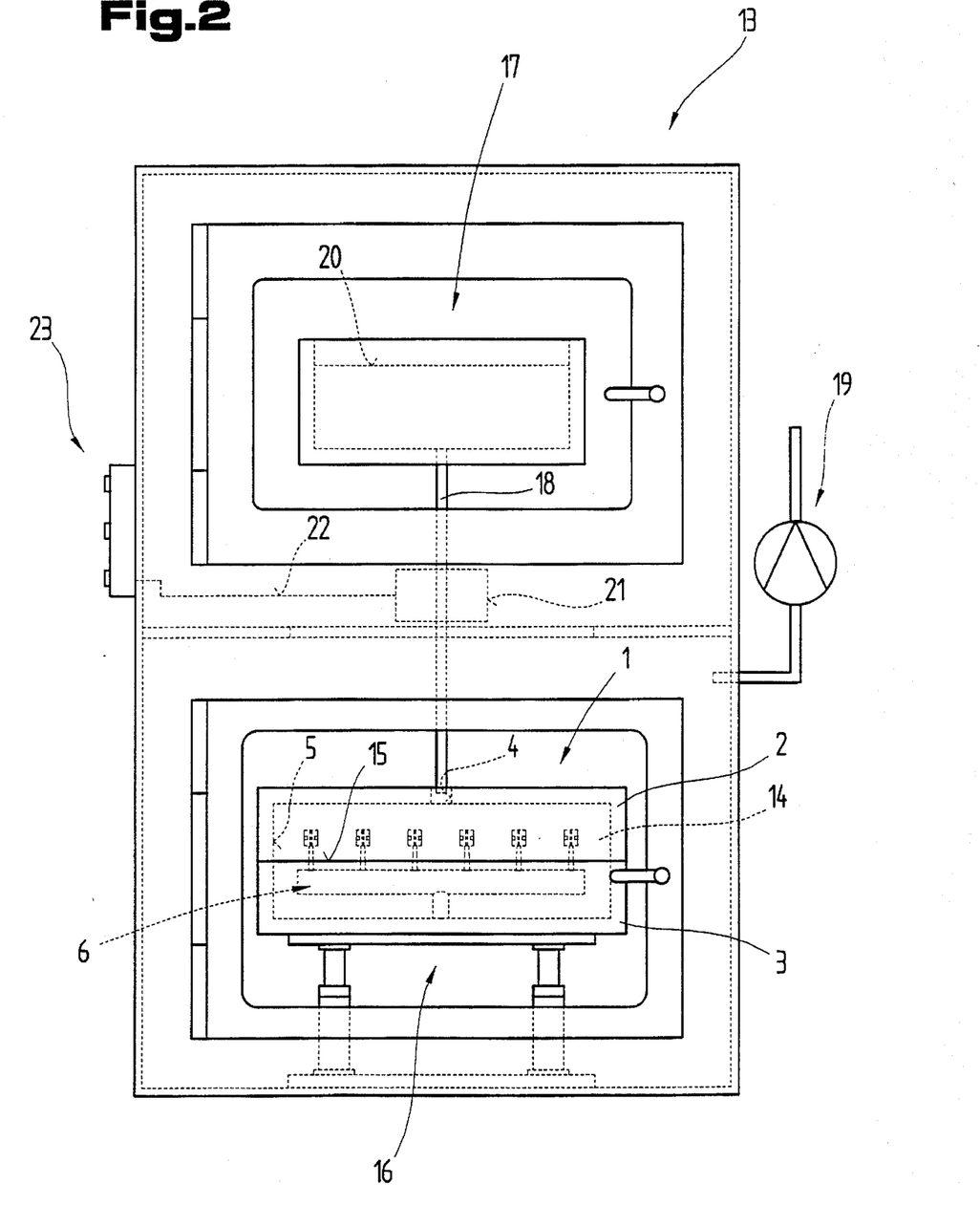
FIG. 2 is a simplified, diagrammatic representation of an installation for the production of the mould for the production of orthodontic component parts.

FIG. 2 shows a diagrammatically simplified installation 13 for the production of a mould 14 in the forming case 1. In order to produce the mould 14, the forming case 1, which consists of a male mould 2 or respectively a female mould 3, is closed, whereby the green model 6 is positioned in the mould cavity 5. Between the male mould 2 or respectively the female mould 3 of the forming case 1, a mould separating plane 15 is formed. In order to facilitate manipulation of the forming case 1 in the installation 13, it is possible to provide a lifter 16.

To produce the mould 14, which preferably consists of a silicone rubber, it is necessary that the casting of the silicone rubber is carded out under a vacuum. Thereby, it is necessary to equip the installation 13 in such a way, that the inner chamber of the installation 13 is evacuated, i.e. the forming case 1 and also a receptacle 17 as well as a feeding pipe 18 which connects the sprue inlet 4 of the forming case 1 with the receptacle 17 are evacuated by means of a vacuum pump 19 which is indicated diagrammatically. Thus, it is ensured that the quantity of the silicone rubber 20 which is brought in from the receptacle 17 via the feeding pipe 18, reaches the mould 14 in a void-free state and without any air bubbles. Moreover, it is possible to dose the quantity of the supplied silicone rubber 20 by means of a regulating device 21 in the feeding pipe 18, whereby the regulating device 21 is connected by means of a line 22 with an input terminal 23 which allows for example to preset the supplied quantity, the feed velocity and other parameters.

After the potting of the silicone rubber 20 into the mould cavity 5, the mould 14 is cured in a heating chamber.

The silicone rubber 20 which is used for the mould 14 is advantageous because it has a high degree of fluidity during the potting process and after curing, a regularly cross-linked rubber having a high shore hardness A and also a high tear resistance and tear propagation strength. This way for example, the shore hardness A of the mould 14 of the cured silicone rubber 20 according to DIN 53 505 is about 50 at 25° C.

Furthermore, the tensile strength is approximately 4.5 MPa and the ultimate elongation is 220%.

FIGS. 3 to 6 show the mould 14 after the green model 6 has been removed.

To remove the green model 6 from the mould 14, the mould 14 must be separated along a predetermined mould plane 24 in a spatially curved parting surface 25. The mould 14 has to be undone from the upper side 26 which is closer to the distribution channel model 9.

Due to the undoing of said mould and the high degree of elasticity of silicone rubber 20, the distribution channel model 9 which is embedded in the mould, can easily be removed, which results in the development of a distribution channel 27 in the mould 14 after said model has been removed. By further undoing the mould 14 down to a depth 28, starting at the upper side 26 into the region of a schematically indicated separating line 29, it is now possible to remove successively from the mould 14 the supply channel model 10 and also the reference component part 8. By virtue of the undoing of the mould 14 along the mould plane 24 or respectively the parting surface 25 resulting therefrom, mould halves 30, 31 are formed starting from the upper side 26 into the region of the separating line 29.

When removing a plurality of supply channel models 10 together with the reference component parts 8 secured thereon, the following steps are to be taken. First, as already described hereabove, the mould 14 is undone along the desired mould plane 24 into the region of the distribution channel model 9 and the latter is removed from the mould 14. Thereby, the distribution channel model 9 is separated from the supply channel models 10. By further undoing the mould 14 to a depth 28, starting at the front face 32 and by swinging open the resulting mould halves 30 and 31, the supply channel model 10 closest to the front face 32 and the reference component part 8 secured thereon can be taken out of the mould 14. After removal of this first green forming unit 33, which consists of a supply channel model 10 and the reference component part 8, the mould 14 is undone further along the mould plane 24 in the direction of a further green forming unit 33 arranged adjacent thereto, by a distance 34, whereby the further green unit 33 can be removed from the mould 14 by an additional swinging open of the two mould halves 30, 31. This step by step process of separating takes place until a further front face 35 opposite the front face 32 is reached. By removing the individual green forming units 33, a supply channel 36 is created in the region of the supply channel model 10 and also a gang of cavities 37 for the production of an orthodontic component part is created in the region of the reference component part 8.

Figure 3:
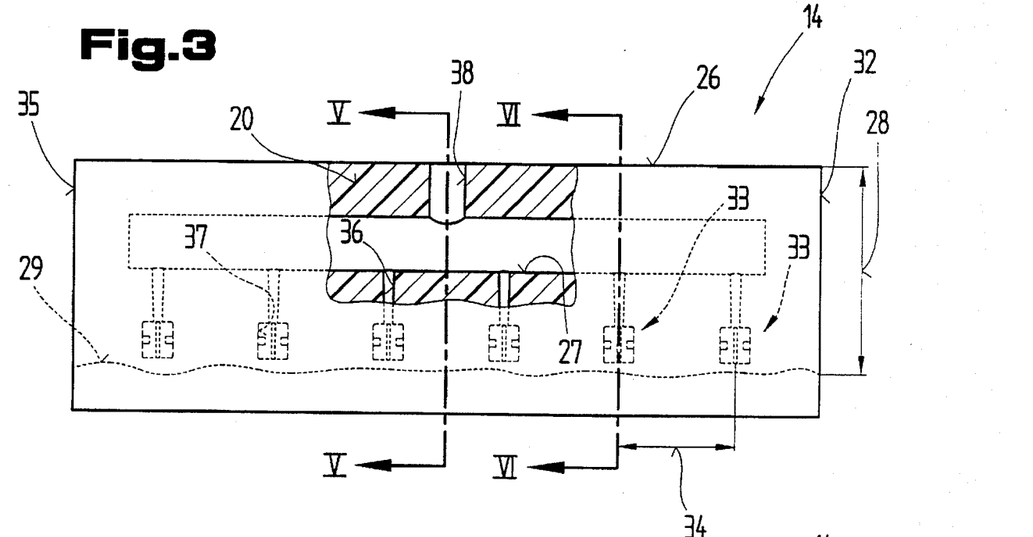
FIG. 3 is a view and simplified, diagrammatic representation of a mould for the production of orthodontic component parts.
Figure 4:
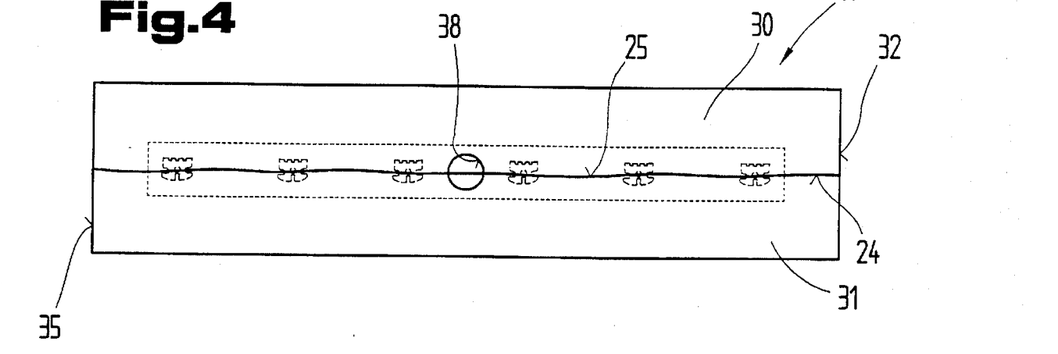
FIG. 4 is a top view of the mould according to FIG. 3.
Figure 5:
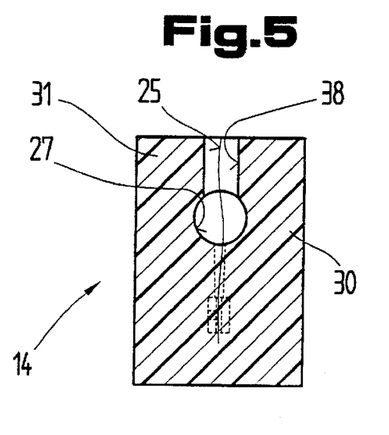
FIG. 5 is a front view, in a section taken along the lines V—V in FIG.3 of the mould according to FIGS. 3 and 4.
Figure 6:
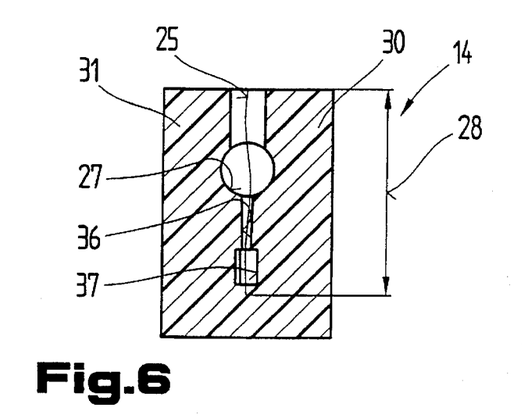
FIG. 6 is a front view, in a section taken along the lines VI—VI in FIG. 3 of the mould according to FIGS. 3 to 5.

In order to fill a casting material into the distribution channel 27 while the mould halves 30, 31 of the mould 14 are closed, it is necessary, starting at the upper side 26, to arrange a sprue channel 38 in the mould 14, which extends into the distribution channel 27. Said sprue channel can be additionally mounted in the mould 14 for example, or, as indicated in FIG. 1 by thin lines, can already be arranged as channel model on the distribution channel model 9.

This way, a mould 14 for the production of orthodontic component parts is created in a simple manner. Due to the waved undoing of the mould 14 along the mould plane 24, a precise mutual self-centering is already achieved when closing the mould halves 30, 31, which prevents the arrangement of further centering elements. The mould 14 manufactured in such a manner, can be produced with relatively simple means which results in a cost-effective portion of the moulds for the production of such component parts. Furthermore, by casting the mould 14 in a vacuum, a precise and void-free projection of the reference component part 8 is achieved in the mould 14.

Figure 7:
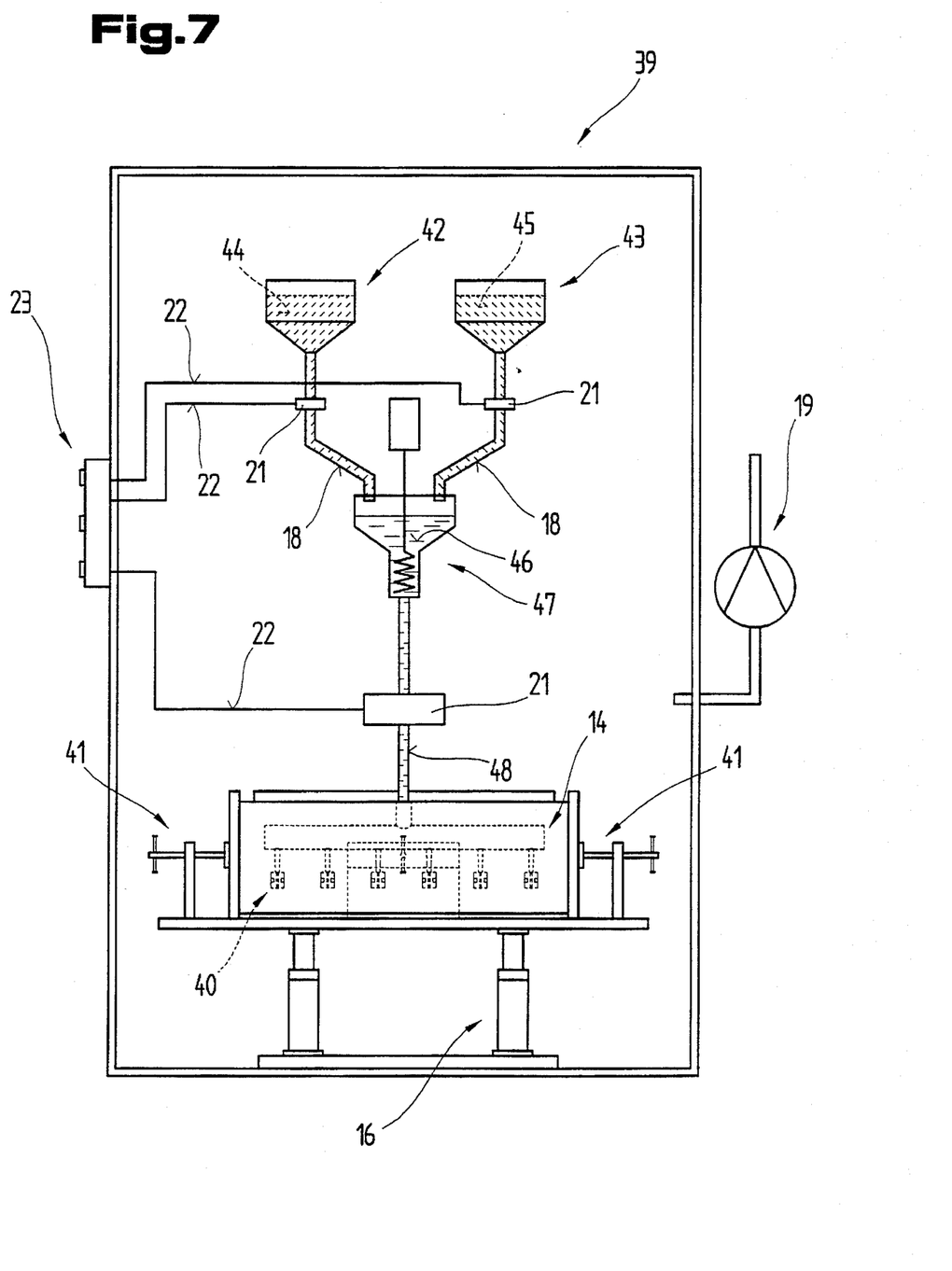
FIG. 7 is an installation for the execution of the method in accordance with the invention for the production of orthodontic component parts.

FIG. 7 shows a schematically indicated installation 39 which serves to cast orthodontic component parts 40 in the mould 14.

To secure the mould 14, in particular the two mould halves 30, 31 which are divided by the parting surface 25 in certain regions of the mould plane 24, for the casting process or to press the two mould halves 30, 31 against each other, said mould is put into a pressing frame 41 and secured therein as schematically indicated. To facilitate the handling of heavier moulds 14 with the corresponding pressing frame 41, it is of course also possible to provide the installation 39 with a lifter 16.

The casting material is a casting resin in the form of a two-component material based on a non-foaming urethane casting resin. The two component parts of the casting resin are stored in containers 42, 43, whereby in the container 42 a schematically indicated binder 44 is included as main component part of the resin, which is based on a polyole basis. In the container 43, on the other hand, is a further component part, namely a hardener 45, which is based on a diphenylmethane -4.4- diisocyanate for example.

The two component parts stored in the containers 42, 43, namely the binder 44 and the hardener 45 of a casting resin 46 are fed into a mixing device 47 through special feeding pipes 18, and the quantity supplied is dosed by regulating devices 21 associated with each feeding pipe 18, which are connected to an input terminal 23 by means of lines 22. The mixing of the binder 44 with the hardener 45 occurs after the appropriate quantity and composition is introduced into the mixing device 47. The feeding of the mould 14 with casting resin 46 takes place by means of a feeding pipe 48 from the mixing device 47 and is monitored by a further regulating device 21 which is also connected to the input terminal 23 by means of a line 22. In order to achieve another precise casting result for the orthodontic component parts 40, it is necessary to evacuate the inner chamber of the installation 39 by means of a schematically indicated vacuum pump 19 thus achieving a problem-free and void-free result.

Care must be taken when processing the binder 44 that the latter is protected against moisture because otherwise carbon dioxide may be released during the reaction when it is mixed with the hardener 45. The resulting carbon dioxide is in a gaseous state and leads to the development of foam in the casting resin 46, which does not allow for problem-free casting results. Therefore, in order to keep the content of moisture and water at a minimum it is advantageous to add a drying agent before use, thereby removing water up to approximately 0.1%. Since the hardener 45 is also reacting to moisture, it must also be treated with care. The mixing ratio between the binder 44 and the hardener 45 is preferably 10:9, whereby a potlife of the mixture of the two components is between 2 to 5 minutes, preferably 3 to 4 minutes. Before the component part 40 is taken out of the mould, it is necessary to expose the mould 14 to approximately 70° C. for a period of about 30 minutes. After this curing period, a hardness of the component part 40 of approximately 80 Shore D, a tensile strength of approximately 60 to 70 N/mm$^2$ and a bending strength of between 100 N/mm$_2$ and 110 N/mm$^2$ is achieved. It can be advantageous if the curing process takes also place in a vacuum.

As casting resins in the different fields of use, differently strong, elastic or transparent types thereof can be used, and can be easily varied to be adapted to certain cases of application. To increase the lifespan of the mould 14, and thereby the number of forming processes, it is advantageous to store the mould 14 after each cast taken for a few hours in the open air or to heat it up shortly at an increased temperature between 50° C. and 100° C. or to warm it up. This way, casting resin particles which entered into the surface of the mould 14 can escape which for the next forming process makes available a mould that is free from impurities and thus a precise cast can be achieved for the component parts 40.

Figure 8:
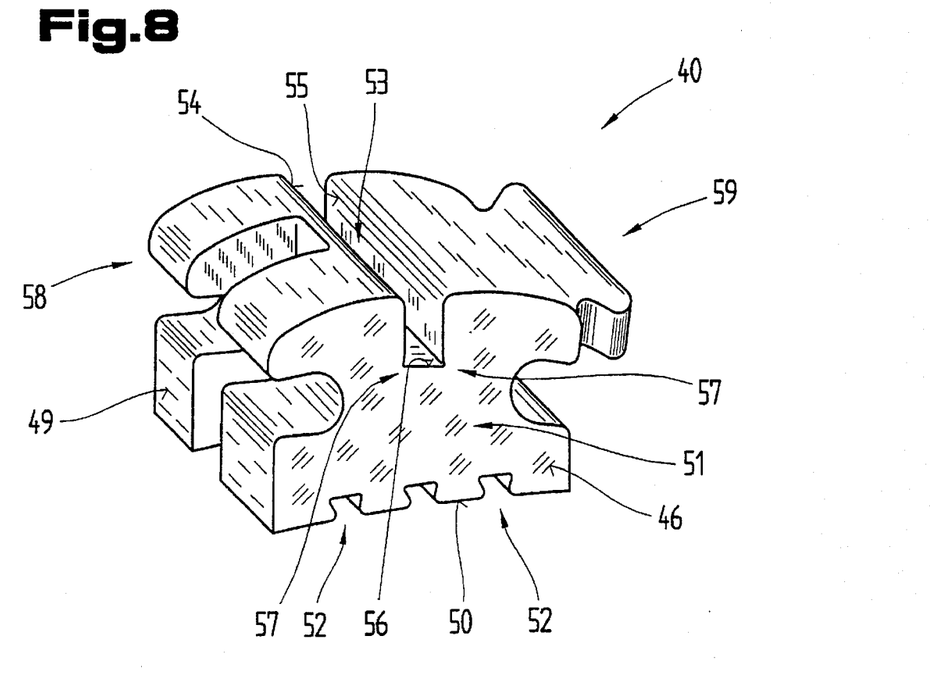
FIG. 8 is a simplified representation, in perspective, of an orthodontic component part produced according to the method in accordance with the invention.

FIG. 8 is a simplified representation, in perspective, of the component part 40 produced according to the invention. As already described hereabove, the component part 40 consists of casting resin 46 which forms a plastic 49, which preferably is a thermoplastic or a thermoset plastic cured to a great extent wherein the polyaddition is terminated at least at body temperature, i.e. about 32°–36° C. Furthermore, it is advantageous, if the component part 40 is formed, as described hereabove, by a strongly cured thermoset plastic, for example polyurethane.

A contact surface 50 of the component part 40, which when applied is facing towards the tooth surface of a user or respectively patient, shows in the direction of a supporting body 51 surface-increasing depressions 52, which in particular, are formed by dovetailed and/or C-shaped slots.

The depressions 52 extend from the contact surface 50 in the direction of a viewing side arranged opposite of the latter into the supporting body 51, and preferably are aligned parallel to a slot 53 arranged on the viewing side. However, it is also possible to design the depressions 52 in the shape of a spherical segment.

The slot 53 has lateral flanges 54, 55 oriented approximately vertically to the contact surface 50 and extends from the viewing side in the direction of the contact surface 50 up to a floor surface 56 in the supporting body 51. A transition area 57 between the lateral flanges 54 or respectively 55 and the floor surface 56 is rounded out, in particular undercut, as shown and described in more detail in FIG. 10.

In a vertical direction to the longitudinal extension of the slot 53 one can see wings 58 or respectively 59 arranged on each side of the slot 53, whereby it is shown that the wing 59 with respect to the contact surface 50 has a convex curvature.

Figure 9:
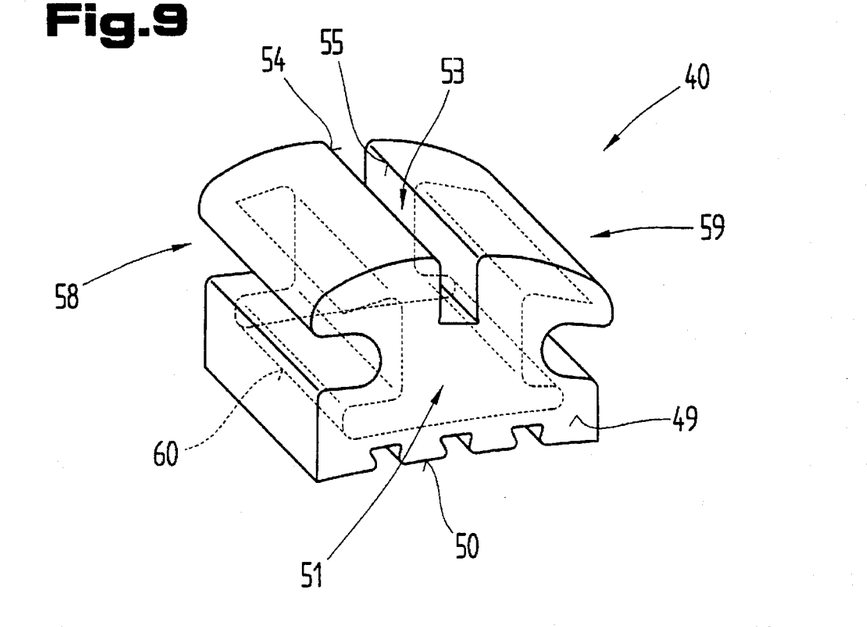
FIG. 9 shows a further orthodontic component part with an additional reinforcing element arranged therein and another wing shape.

FIG. 9 shows another embodiment of the orthodontic component part 40 in which the same reference numbers are used for the same parts.

In order to reinforce the wings 58 or respectively 59 of the orthodontic component part 40, a reinforcement element 60 is arranged in the supporting body 51, which, surrounded from all sides, is embedded in the plastic 49. This serves especially for a design which makes the embodiments of the wings 58 or respectively 59 stiffer or stronger with respect to the supporting body 51. The embodiment of the slot 53 with its lateral flanges 54, 55 or respectively the contact surface 50 can take place for example as described hereabove.

Figure 10:
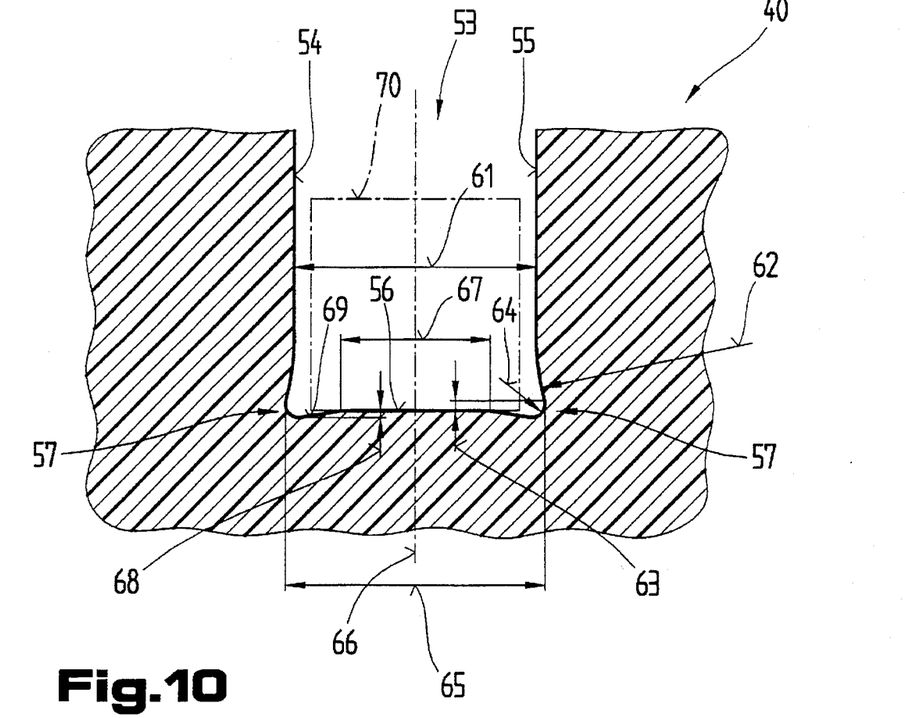
FIG. 10 is a greatly enlarged representation of the orthodontic component part in the vicinity of the slot.

FIG. 10 shows a detailed embodiment of the slot 53 of the component part 40 in an enlarged scale. The slot 53 has lateral flanges 54, 55, as described hereabove, which in the transition area 57 when undercut and curved, end in the floor surface 56. Between the lateral flanges 54, 55 which are arranged parallel to one another, the slot 53 has a width 61, which, on both sides towards the transition area 57, is designed to be widening about a transition radius 62 and extending at a distance 63 above the floor surface 56 in a smaller radius 64 which is in the opposite direction, whereby it has in this region of the slot 53 its largest width 65.

Starting from a longitudinal central axis 66 of the slot 53, the floor surface 56 is oriented vertically to the lateral flanges 54, 55, whereby a width 67 of the plane-surfaced floor surface 56 is arranged centrically to the longitudinal central axis 66. The radius 64 extends to a depth 68 below the floor surface 56 and is each time connected by an ascending transition face 69 in the direction of the longitudinal central axis 66 with the two marginal portions of the floor surface 56.

Due to this special embodiment of the transition areas 57 of the slot 53, it is possible, as indicated by dash-and-dot lines, to guide a tensioning wire 70 which has an approximately square cross-section, into the slot 53.

Figure 11:
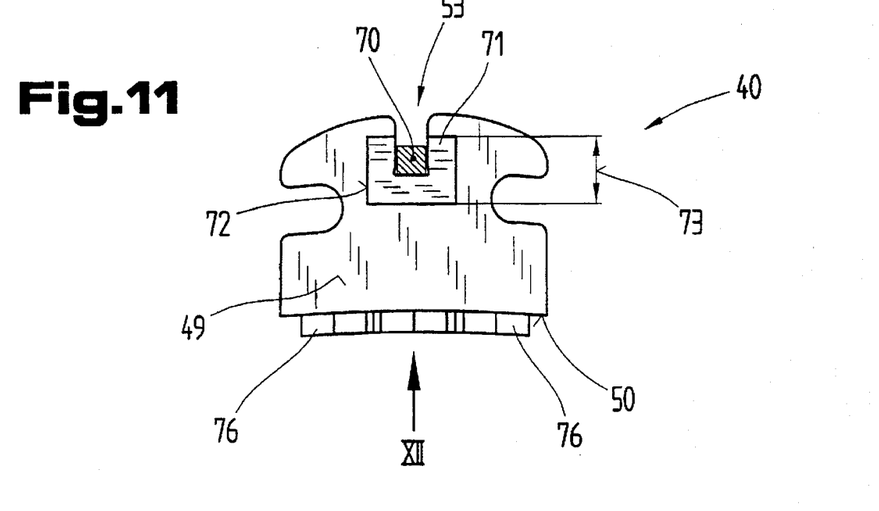
FIG. 11 is a side view of another embodiment of the orthodontic component part with a lining element in the vicinity of the slot.
Figure 12:
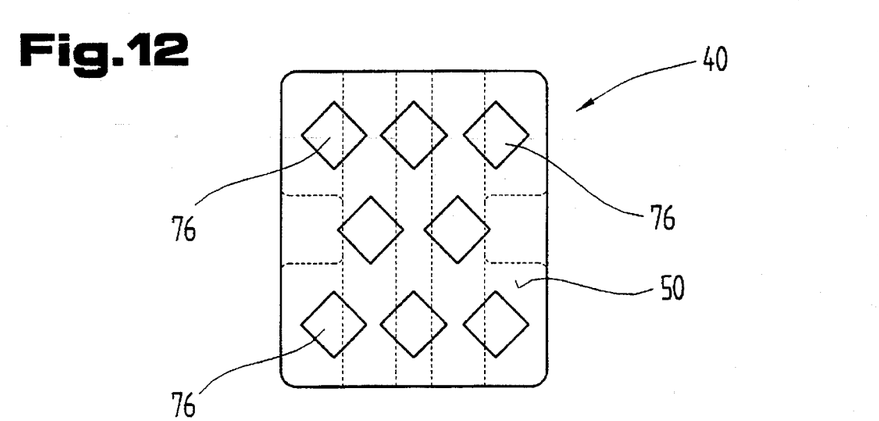
FIG. 12 is a bottom view according to arrow XII in FIG. 11 of the component part according to FIG. 11.
Figure 13:
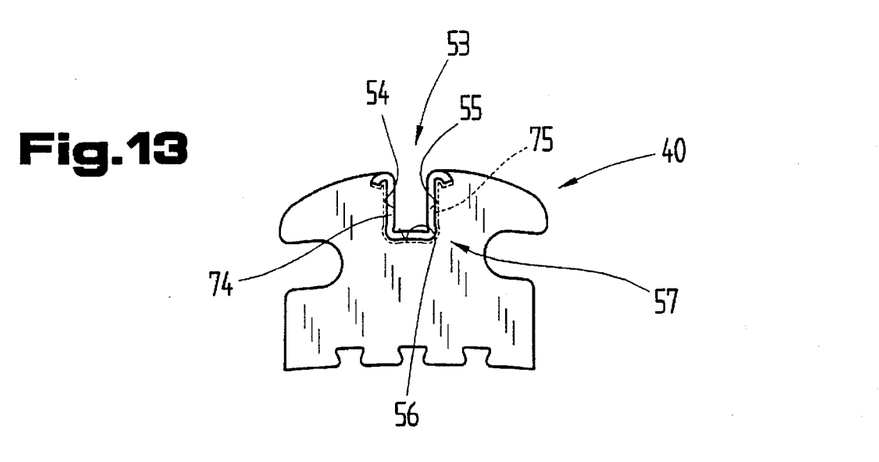
FIG. 13 is another embodiment for the reinforcement of the slot of an orthodontic component part.

FIGS. 11 to 13 show another embodiment of the orthodontic component part 40 which consists of a plastic 49, in which the same reference numbers are used for the same parts.

In order to minimize the friction between the tensioning wire 70, also known as ligature wire, and the slot 53 of the orthodontic component part 40, it is possible to arrange a lining element 71 in the root area of the slot 53, which, for example before the casting resin 46 is poured into the mould 14 is introduced into the latter. The lining element 71, may consist for example of zircon oxide and in the region of its surfaces 72 facing towards the supporting body 51 or respectively the plastic 49, is formed onto the latter or respectively connected to it in a frictional and/or formlocking manner.

Furthermore, it is advantageous if a height 73 of the lining element 71 is not extending into the region of the viewing side of the orthodontic component part 40 and is surrounded by plastic 49 in the upper region of the slot 53, i.e. in the region of the viewing side. This ensures a tight grip in the orthodontic component part 40.

It is, of course also possible, as indicated in FIG. 13, to provide the entire slot 53 in its longitudinal extension and in the region of its lateral flanges 54, 55 or respectively floor surface 56 and transition areas 57 with a friction-reducing coating 74. This coating 74 can be formed on the plastic 49 either directly during the production process, i.e. when the component part 40 is poured into the form 14. It is, however, also possible to secure the coating 74 or respectively the lining element 71 on the orthodontic component part 40 by an adhesive layer 75 which is indicated by broken lines.

As can be seen further from FIGS. 11 and 12, in order to enlarge the surface of the connection faces it is possible to enlarge on the contact surface 50, that is to say that surface which is associated with the tooth surface of the patient, the projections 76 which protrude in the direction of the tooth surface. Thereby, the projections 76, as can be seen best from FIG. 12, can be constructed for example in the shape of a rhombus. It is of course also possible to design the projections 76 in the shape of a spherical or semicircular segment, so as to enlarge the remaining free space between the projections 76 for receiving the bonding agents between the orthodontic component part 40 and the tooth surface.

Figure 14:
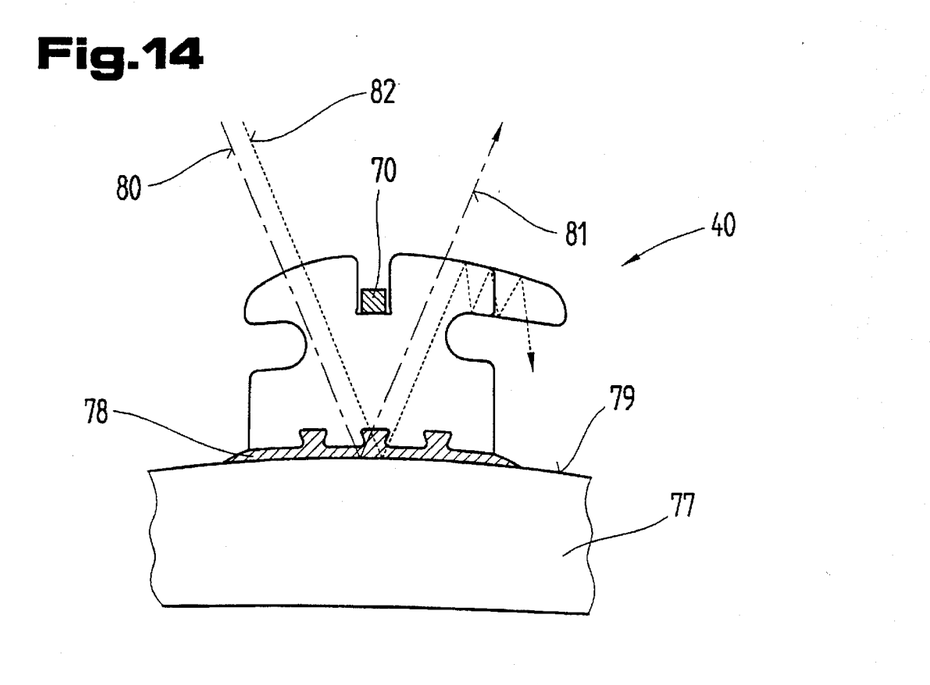
FIG. 14 is a front view and a simplified, diagrammatic representation of the orthodontic component part in its position of use when secured to a tooth.

FIG. 14 shows the orthodontic component part 40 in a position of use on a tooth 77, whereby the component part 40 is secured to a tooth surface 79 by means of a connecting layer 78.

To reduce the visibility of the orthodontic component part 40 on the tooth 77, it is advantageous if the plastic 49 has an in-line translucence between 5% and 90% at a thickness of 0.5 mm. This way, one achieves that the beams of light 80 which enter the orthodontic component part 40 penetrate up to the tooth surface 79 and are reflected by the latter, and a reflected light beam 81 corresponding to the color of the tooth 77 emerges the component part 40. Due to the fact that only a very small portion of the beams of light 80 entering the component part 40 are absorbed, one has the visual impression that the orthodontic component part 40 takes on the color of the tooth 77 which is the particular coloring of teeth of each user. Thus, an orthodontic component part 40 has been created in a simple manner, which, on the one hand is easy to produce and on the other hand, is optically very discreet for the user.

If the desired composition of the casting resin 46 is to be changed accordingly, the emergence of reflected light beams 81 can be reduced or stopped, as is schematically indicated by a beam of light 82 drawn in broken lines. This causes the inherent coloring of the component part 40 to come to the fore and a clear optic visibility with respect to the tooth 77 takes place.

The degree of radiation transmission of a material is defined by the degree of translucence, which is the ratio resulting from the intensity of the beam allowed to pass through and the intensity of the entering beam, and refers to the radiation of a certain wave length and a specimen of a certain thickness These variables are established by the following formula $$I/I_0 = ke^{-ad}$$

in which "$I/I_0$" are the intensities of the beam passed through and of the entering beam, "d" is the thickness of the specimen, "a" is the absorption coefficient and "k" a constant which can be determined from the index of refraction of the material, which are put in relation to one another. Thereby, the cone angle of the entering beam and the cone angle of the beam which has passed through must be mentioned.

Measuring of the transmission degree can take place by means of a laser beam at a wave length of 0.63 mm so that the cone angle of the entering beam is close to zero. The cone angle of the beam which has passed through, which serves for determining the intensity of the passed through beam, can be 60° for example. This way, a transmission degree, i.e. an in-line translucence can be defined.

It is of course also possible, to carry out this in-line translucence by means of a Perkin-Elmer-Lambda-spectrophotometer, for example of the type 9UV/VIS/NIR, wherein the wave range can be between 400 nm and 800 nm.

Preferably, the thickness of the specimen is 0.5 g 0.005 mm whereby high quality surface processing is to be provided, that is to say a very fine polishing has to take place in order to avoid any reflection of the light due to irregularities on the surface of the specimen which may change the measuring result to a great extent. Basically, it has to be taken into account that the measuring of the in-line translucence is a difficult problem since the quantity of light used to expose the specimen to radiation is put into relation to the quantity of light of a given wave length, which emerges from the specimen. The difference in these two light quantities lies in the fact that the irradiated light is deviated due to its irregularities in the specimen, such as grains, grain boundaries and the like, and is therefore dispersed. This deviation and dispersion depends essentially on the size and the form of the irregularities, and a measuring of the light distribution becomes difficult if its size is in the region of the wave length which has been used for this measuring test. Therefore, each test sample has to be produced with two surfaces that are plane-parallel to each other, which have to be polished to a predefined surface roughness.

To measure the in-line translucence, the test sample is exposed to a directed or parallel concentrated beam of light with little beam spread, which is oriented perpendicular to the surface. A partial loss of the radiation intensity is caused by the transition of the radiation of air onto the test sample due to the different refractive index between the air and the test sample. The light intensity entering the test sample is then deviated into different directions by irregularities. Therefore, the permitted angle of incidence of the radiation with respect to the measuring device is an essential factor for the determination of the in-line translucence. The greater the permitted angle of incidence on the measuring device, the greater is the measured in-line translucence for the same test sample.

This is why for all testing, the angle of incidence of light of the light beam falling onto the test sample and also the angle of emergence of light of the emerging beam of light shall be identical.

Preferably, an angle of 3° can be accepted as an angle of incidence for example. Thereby it is advantageous to use a beam directed onto the test sample which has a width of 0.2 mm and a height of 0.5 mm and to provide a screen with a diameter of 1 mm or respectively 0.5 mm.

However, it is also possible to set the angle of incidence of the beam to be let through at approximately 60°.

It is essential for the present invention, that a color absorption of the bracket is optically reached when it corresponds to the color of the tooth situated thereunder, if a translucence is very high, for example of between 70% and 90%, since the majority of the in-line transmittance of the light arrives vertically on the tooth and is reflected by the latter towards the outside, so that an observer can essentially only recognize the color of the tooth, and the orthodontic component part respectively the bracket seems to take on the color of the tooth.

In component parts, which compared to objects situated behind them, the color of which they should take on, are very small, it is possible that an in-line translucency of 60%–80% or 30%–70% is enough, since a great portion of the light reflected into different sides and not in a straight direction, can also be retransmitted back, which causes the component part, which has been mounted in addition, to predominantly take on the color of the background making it nearly invisible.

Low translucence values of for example 5 to 30% can be used to provide such component parts for example with an inherent color, whereby the portion of the inherent color of the component parts will be predominant for the observer. Due to the small amount of light reflected by the background, the effect on the surface thereunder will be very small, or will be sufficient when the bracket is appropriately colored according to the base material in order to balance nuances of color if needed.

A better result is achieved in component parts which are approximately adapted to the color of the background, if the in-line translucence is between 10 and 35%. This achieves a good adaptation between the coloring of a component part and a portion of color of the base body.

Figure 15:
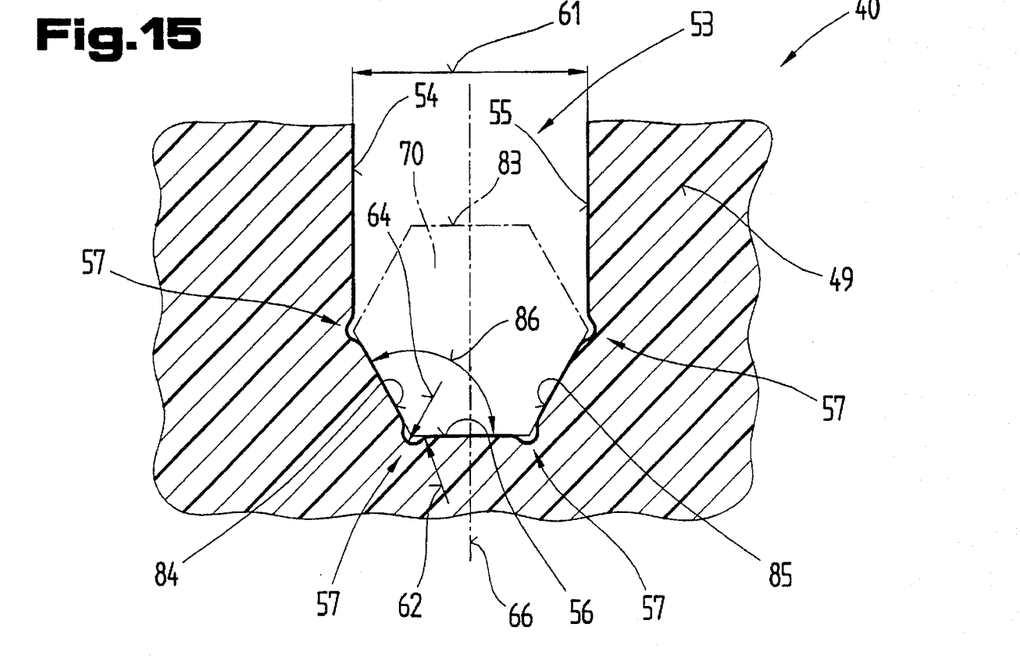
FIG. 15 is a greatly enlarged representation of another embodiment of the cross-section of the slot.
Figure 16:
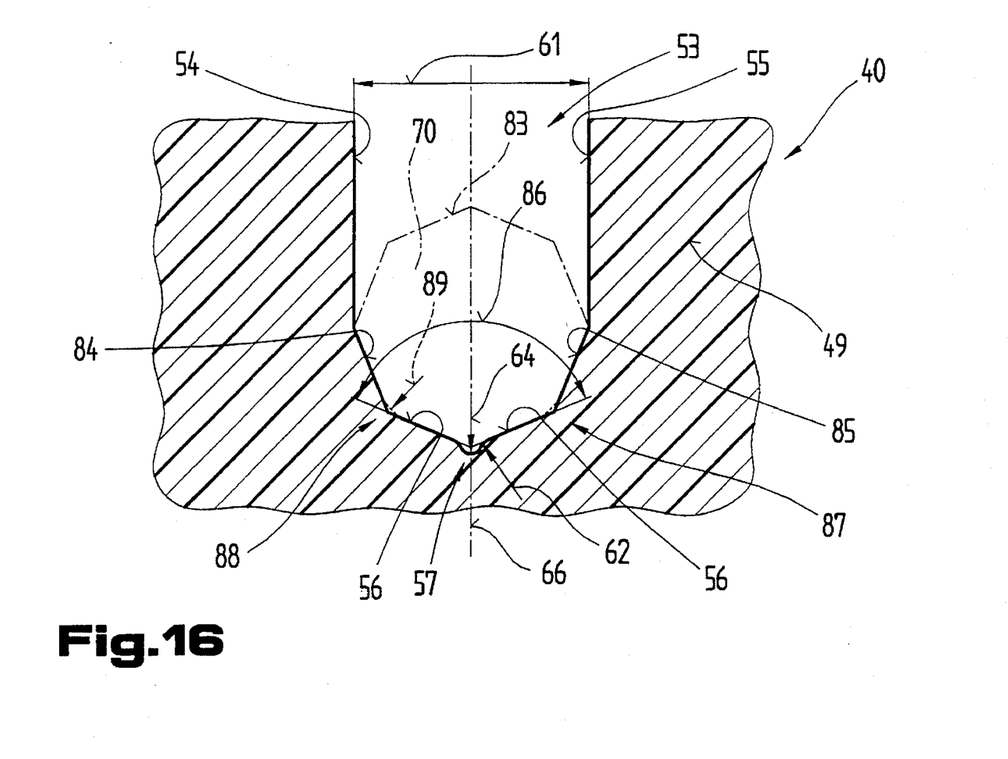
FIG. 16 is a greatly enlarged diagrammatic representation of a further embodiment of the slot for the orthodontic component part.

FIGS. 15 and 16 show a further embodiments or respectively cross-sectional shapes of the slot 53 in the component part 40 at a larger scale in which the same reference numbers are used for the same parts.

This slot 53 has lateral flanges 54, 55, which in this embodiment are arranged symmetrically to the longitudinal central axis 66 at a distance 61 apart from one another. These lateral flanges 54, 55 extend thereby essentially about normal with respect to the contact surface 50 of the orthodontic component part 40. It is however also possible to arrange the lateral flange 54, 55 at any angle to the contact surface 50, in order to adapt in a simple manner the holding force of the tensioning wire 70 with respect to the contact surface 50 to the different conditions of use.

As can be seen from the representation in FIG. 15, the tensioning wire 70, shown schematically in dash-and-dot lines, has a hexagonal cross-sectional shape and forms therefore the lateral faces 83.

According to these lateral surfaces 83 of the tensioning wire 70, the floor area of the slot 53 presents the floor surface 56, which by means of the intermediate faces 84, 85 oriented towards the cross-sectional shape of the tensioning wire 70, is connected to the lateral flanges 54, 55. By virtue of the hexagonal cross-sectional shape of the tensioning wire 70, an angle 86 is forming between the floor face 56 and the two intermediate faces 84, 85, which, in the present example is 120°.

As can be seen further at the transition areas 57 between the lateral flanges 54, 55 and the intermediate faces 84, 85 or respectively between the latter and the floor surface 56, the latter present a rounding or respectively undercutting, in order to prevent by starting from the corner section of the tensioning wire 70, which is forming between the lateral faces 83 of the latter, an impact effect on the component part 40. The undercutting has a radius 64 in the respective corner section of the tensioning wire 70, which is rounded out by means of the transition radii 62 towards the adjacent faces or flanges. This way, the occurrence of impact effects in the case of stress of the tensioning wire 70 with respect to the plastic 49 of the component part 40 is reliably prevented.

FIG. 16 shows another cross-sectional shape of the tensioning wire 70, which, in this exemplary embodiment has an octagonal cross-section. The slot 53 of the component part 40 has again lateral flanges 54, 55 which are arranged at a distance 61 from one another, which, essentially are again oriented perpendicular to the contact surface 50 of the orthodontic component 40.

The floor region of the slot 53 is designed according to the octagonal cross-sectional shape of the tensioning wire 70 which is indicated schematically by dash-and-dot lines. The tensioning wire 70 has lateral faces 83, to which the two floor surfaces 56 which are about an angle to one another and also the intermediate faces 84, 85 are adapted with respect to their course or respectively orientation. Furthermore, this embodiment shows that the transition area 57 between the two floor surfaces 56 is rounded out or respectively undercut, whereby the undercutting has a radius 64. The transition radius 62 arranged between the radius 64 and the two floor surfaces 56 which are bordering it on both sides, serves for a better rounding out of the undercutting in order to prevent or reduce impact effects from the corner region of the tensioning wire 70 when the orthodontic component part 40 is under stress. It is, however, also possible to use any other curved or line shape instead of the transition radius 62 or respectively the radius 64.

Furthermore, it can be seen from the transition areas 87, 88 between the two floor surfaces 56 and the subsequent intermediate faces 84, 85 that they may also be designed without any undercutting or rounding out. To reduce the impact effect or stresses in these transition areas 87, 88, or to avoid them, it is possible to design the edge region between the lateral faces 83 of the tensioning wire 70 having a rounding 89 indicated by a broken line, which in this case also prevents the above described impact effect in the transition areas 87, 88.

Instead of the cross-sectional shapes of the tensioning wire 70 shown in the present example, it should be noted, that also any desired cross-sectional shape of the tensioning wire 70 may be used, and that the embodiment according to FIGS: 10, 15 and 16 has been selected only as an example. It is therefore also possible, to select any polygonal, regular or irregular cross-sectional shape for the tensioning wire 70, respectively to design it in an oval or round shape. This depends each time on the required purposes of use of the orthodontic component part and can be chosen freely. Also the embodiment of the individual transition areas 57 or respectively 87, 88 is only shown by way of example, whereby the roundings or undercuttings can present any geometrical shape or can be completely eliminated.

Finally, it should be noted that in the embodiments described hereabove, single parts have been represented unproportionally enlarged, in order to improve the understanding for the solutions according to the invention. Furthermore, individual parts of the above described combination of features of the individual embodiments can also form their own, inherent solutions according to the invention in connection with the individual features from other exemplary embodiments.

In particular, the individual embodiments shown in FIGS. 1; 2; 3, 4, 5, 6; 7; 8; 9; 10; 11, 12; 13; 14; 15; 16 can form the object of own solutions in accordance with the invention. Relating tasks and solutions in accordance with the invention are apparent from the detailed descriptions of these Figures.

What is claimed is:

1. An orthodontic component part having a body made of a plastic produced by an addition polymerization terminated at a temperature corresponding at least to about normal human body temperature.

2. The orthodontic component part of claim 1, wherein the plastic is a cross-linked thermosetting plastic.

3. The orthodontic component part of claim 2, wherein the thermosetting plastic is polyurethane.

4. The orthodontic component part of claim 1, wherein the plastic is a thermoplastic plastic.

5. The orthodontic component part of claim 1, further comprising a reinforcement element embedded in the plastic body.

6. The orthodontic component part of claim 1, wherein the plastic body defines a slot having side walls and a bottom wall, the slot extending in a longitudinal direction towards a contact surface of the plastic body with a surface of a tooth on which the orthodontic component part is to be mounted.

7. The orthodontic component part of claims 6, further comprising a friction-reducing element lining at least a portion of the side and bottom walls of the slot.

8. The orthodontic component part of claim 6, wherein the slot has a polygonal cross-section.

9. The orthodontic component part of claim 6, wherein the slot walls have adjoining portions interconnected by rounded, undercut transition areas.

10. The orthodontic component part of claim 6, wherein the plastic body further comprises at least one wing extending at least in one direction from the slot perpendicularly to the longitudinal direction, the wing having a convexly curved surface facing the contact surface of the plastic body.

11. The orthodontic component part of claim 6, wherein the contact surface of the plastic body has surface-enlarging connecting faces.

12. The orthodontic component part of claim 11, wherein the contact surface has projections defining depressions therebetween to constitute the connecting faces.

13. The orthodontic component part of claim 12, wherein the depressions have a dovetailed cross section.

14. The orthodontic component part of claim 1, wherein the plastic body has an in-line translucence of 5% to 90% at a thickness of 0.5 mm.

15. A method for the production of an orthodontic component part, which comprises the steps of
   (a) affixing a reference orthodontic component part to a sprue channel model to provide a green model,
   (b) positioning the green model in a form casing comprised of a male mold and a female mold separated by an undulated parting plane between the male and female molds so that the sprue channel model is positioned in the parting plane, (c) filling the form casing with a silicone cast resin under vacuum and curing the silicone cast resin until it has achieved form stability to provide a mold, (d) removing the cured silicone cast resin mold from the form casing, (e) separating at least a portion of a cross-sectional surface of the mold along the parting plane, (f) removing the green model from the silicone cast resin mold to form a corresponding mold cavity in the mold, (g) filling the mold cavity under vacuum with a plastic-forming casting resin, (h) initiating an addition polymerization of the casting resin and terminating the addition polymerization upon reaching a temperature corresponding at least to about normal human body temperature to obtain a form-stabilized orthodontic component part, and (i) removing the orthodontic component part from the mold cavity.

16. The method of claim 15, further comprising the step of heating the mold during the addition polymerization.

* * * * *